(12) United States Patent
Rajaraman et al.

(10) Patent No.: US 7,608,725 B2
(45) Date of Patent: Oct. 27, 2009

(54) PROCESSES FOR NITRATION OF N-SUBSTITUTED IMIDAZOLES

(75) Inventors: Shanthi Rajaraman, Howell, NJ (US); Umar Yaqub, Brigantine, NJ (US)

(73) Assignee: The Richard Stockton College of New Jersey, Pomona, NJ (US)

( * ) Notice: Subject to any disclaimer, the term of this patent is extended or adjusted under 35 U.S.C. 154(b) by 267 days.

(21) Appl. No.: 11/746,727

(22) Filed: May 10, 2007

(65) Prior Publication Data

US 2008/0045722 A1 Feb. 21, 2008

Related U.S. Application Data

(60) Provisional application No. 60/799,487, filed on May 11, 2006.

(51) Int. Cl.
*C07D 233/66* (2006.01)
*A61K 31/4168* (2006.01)
(52) U.S. Cl. .................................. 548/327.5; 514/398
(58) Field of Classification Search .............. 548/327.5; 514/398
See application file for complete search history.

(56) References Cited

FOREIGN PATENT DOCUMENTS

CN 1461749 12/2003
JP 2001122861 5/2001

OTHER PUBLICATIONS

Davis et al, "New Syntheis of 2-Nitroimidazoles," J. Het. Chem. (1982), vol. 19, pp. 253-256.*
Brezden C.B. et al., Biochem. Pharmacol., vol. 48, pp. 361-370 (1994).
Brown, J.M. et al, "Exploiting Tumour Hypoxia In Cancer Treatment," Nature Reviews, vol. 4, pp. 437-447 (Jun. 2004).
Chauviere, G. et al., J. Med. Chem., vol. 46, pp. 427-440 (2003).
Cowan, D.S.M et al., Br. J. Cancer, vol. 70, pp. 1067-1074 (1994).
Davis et al., J. Heterocyclic Chem., vol. 19, pp. 253-256 (Mar.-Apr. 1982).
Denny, W.A. et al., J. Med. Chem., vol. 29(6), pp. 879-887 (1986).
Grimmett, M.R., Heterocyclic Chem., vol. 27, p. 241-326 (1980).
Hay et al., J. Med. Chem., vol. 46, pp. 5533-5545 (2003).
Jaffar et al., Adv. Drug Del. Rev., vol. 53, pp. 217-228 (2001).
Kasai et al., Bioorg. Med. Chem., vol. 9, pp. 453-464 (2001).
Lin et al., J. Med. Chem, vol. 15, pp. 1247-1252 (1972).
Naylor et al., Mini Rev. Med. Chem., vol. 1, pp. 17-29 (2001).
Papadopoulous et al., Bioorg. Med. Chem., vol. 14, pp. 1523-1525 (2004).
Rauth, A.M. et al., Int. J. Radiation Oncology Biol. Phys., vol. 42, pp. 755-762 (1998).
Shimamura et al., Brit. J. Cancer, vol. 88, pp. 307-313 (2003).

* cited by examiner

*Primary Examiner*—Joseph K. McKane
*Assistant Examiner*—Janet L Coppins
(74) *Attorney, Agent, or Firm*—Lowenstein Sandler PC

(57) ABSTRACT

The present invention relates to a process for making 2-nitroimidazoles that involves the selective nitration of N-substituted imidazoles.

22 Claims, No Drawings

PROCESSES FOR NITRATION OF N-SUBSTITUTED IMIDAZOLES

CROSS-REFERENCE TO RELATED APPLICATION

The present application claims the benefit of U.S. Provisional Application Ser. No. 60/799,487, filed May 11, 2006 which is incorporated by reference in its entirety.

FIELD OF INVENTION

The present invention relates to a process for making 2-nitroimidazoles that involves the selective nitration of N-substituted imidazoles.

BACKGROUND OF THE INVENTION

Imidazoles are an important class of compounds that are present in many drugs and biologically active molecules. In particular, nitroimidazoles have diverse biological and medical applications, ranging from use as, for example, antibacterial and antifungal agents to cancer tissue markers and chemotherapeutic agents. Nitroimidazoles also are used widely as hypoxia selective cytotoxic agents. See e.g., Rauth, A. M. et at *Int. J. Radiation Oncology Biol. Phys.* (1998) 42; 755-62. Hypoxia—a reduction of oxygen supply to tissue below physiological levels despite adequate perfusion of the tissue by blood—is a condition present in many solid tumors where the cells of the tumors are deficient in oxygen. In solid tumors, the hypoxia regions often surround areas of necrosis, which are areas of dead cells or tissues resulting from injury or disease that occur usually in a localized area of the body. Hypoxia also is observed in arthritic joints, inflammatory bowel disease and other conditions.

Because of its association with tumors, hypoxia is a very important diagnostic tool for tumor onset. Further, the design and development of drugs selectively toxic towards hypoxic cells are important because, for example: (1) tumor cells are severely more hypoxic than normal cells; (2) radiotherapy fails in hypoxic cells, and thus, as a treatment for solid tumors, since hypoxic cells are deficient in oxygen, which is a radiation sensitizer (i.e., an agent that makes cells and tissue susceptible to the effects of radiation); (3) bioreductive hypoxia selective cytotoxins (i.e., compounds that are specifically targeted towards, and toxic to, hypoxic tissues) kill hypoxic cells, which are resistant to most anticancer drug treatments; and (4) hypoxia in tumors often promotes a more malignant phenotype. See e.g., Brown, J. M. and W. R. Wilson, *Nature Reviews* (June 2004) 4: 437-47. Therefore, hypoxia-selective drugs and prodrugs that selectively release an active agent in hypoxic tissues are important to the treatment, prevention and control of tumors, such as solid tumors, and other conditions associated with hypoxia. As used herein, the terms "drug" and "active agent" refers to (A) articles recognized in the official United States Pharmacopoeia, the official Homoeopathic Pharmacopoeia of the United States, or any official National Formulary, or any supplement to any of them, (B) articles, including, e.g., chemical compounds or biologicals, intended for use in the diagnosis, cure, mitigation, treatment, or prevention of disease in man or other animals; and (C) articles intended to affect the structure or any function of the body of man or other animals, and (D) articles intended for use as a component of any article specified in clause (A), (B), or (C). As used herein, the term "biologicals" refers to medicinal preparations made from living organisms and their products, including, e.g., serums, vaccines, antigens, antitoxins, and the like. As used herein, the term "prodrug" refers to a reversibly modified agent that usually is inactive in itself, hut which releases an active agent when metabolized in the body. Often, endogenous enzymes act upon a prodrug thereby activating it upon reduction, and thus, triggering the hitherto latent functionality. A prodrug can (1) increase or decrease the metabolic stability of the active agent, (2) mask or reduce side effects and toxicity of an active agent, and (3) improve transport characteristics, solubility properties and the flavor of the active agent.

A specific type of prodrug is that known as a bioreactive drug or a bioreductively activated drug, which is an agent that is reduced in hypoxic regions (such as solid tumours) usually by one electron reduction (Denny, W. A. and W. R. Wilson, *J. Med. Chem.* (1986) 29(6): 879-87). The use of bioreactive drugs was investigated first by Lin et al in 1972 (*J. Med. Chem.* 15: 1247-52). If the reduced species of the bioreductive drug is the active form, then often the drug will have relatively few side effects. Ideally, the reduction will be reversible so that if the agent is reduced in an oxic region (i.e., an oxygen-containing region), it is oxidized back to a non-active form by molecular oxygen. As used herein, the term "reduced" or "reduction" refers to the loss of an oxygen atom from a compound with a gain of electrons by the compound, or a decrease in oxidation number (oxidation state) of a compound. As used herein, the term "oxidized" or "oxidation" refers to the addition of oxygen to a compound with a loss of electrons, or an increase in oxidation number (oxidation state) of a compound. As used herein, the phrase "oxidation number" or "oxidation state" refers to the number of electrons that must be added to or subtracted from an atom in a combined state to convert it to the elemental form, i.e., the form relating to, being or existing as an uncombined chemical element.

Bioreductively activated drugs are widely in demand for their specific and selective targeting of diseased tissues. Nitroimidazoles have been used as prodrugs for many years. The use of nitroimidazoles in anti-tumor therapy stems from the differences observed in the environment of, and the physiological concentration of molecular oxygen in, tumor versus normal tissues. Tumor cells reside in a much more acidic environment than normal cells, and as discussed previously, are severely more hypoxic than normal cells. In the context of tumor therapy and diagnosis of hypoxia, although 4- and 5-nitroimidazoles are studied, 2-nitroimidazoles are by far, the most extensively studied. See e.g., Shimamura, et al. *Brit. J. Cancer* (2003) 88: 307-13; Kasai et al. *Bioorg. Med. Chem.* (2001) 9: 453-64; Papadopoulou et al. *Bioorg. Med Chem.* (2004) 14: 1523-25. In particular, 2-nitroimidazoles have significantly higher reduction potentials (about −418 mV) as compared to unsubstituted nitrobenzene (about −486 mV) and hence, are known to be selective to hypoxic regions of tumors. The 2-nitroimidazoles, therefore, have been identified as one of the three structurally different classes of bioreactive drugs with selective toxicity towards hypoxic cells; the mitomycins and benzotriazine dioxides being the other two classes.

The 2-nitroimidazoles, mitomycins and benzotriazine dioxides, as bioreactive drugs, are activated selectively in the absence of oxygen to reactive intermediates that can damage deoxyribonucleic acid (DNA). In the case of 2-nitroimidazoles, several reactive reductive intermediates—namely, the nitroso and hydroxylamine intermediates, have been isolated and their interaction with DNA and cellular thiols have been assessed at the molecular level. See e.g., Cowan, D. S. M., et al. *Br. J. Cancer* (1994)70: 1067-74; Brezden, C. B., et al. *Biochem. Pharmacol* (1994) 48: 361-70. As used herein, the phrase "reductive intermediate" refers to an intermediate as defined below that has the ability to remove oxygen from a compound, or cause the compound to react with hydrogen or form a hydride, or to undergo an increase in the number of electrons. This has led to a realization that the target for cell killing by these bioreductive drugs may have a cellular redox component (i.e., a change in oxidation state component) and a direct DNA damage component, resulting in apoptotic cell death, which is one of the main types of programmed cell death that involves the deliberate relinquishment of life by a cell by a programmed sequence of events (i.e., "a cell suicide mechanism"). Derivatives of 2-nitroimidazole attached to DNA intercalating moieties have been synthesized to determine the degree to which targeting 2-nitroimidazoles to DNA affects the efficacy of 2-nitroimidazoles as radiosensitizers and hypoxic cell toxins. As used herein, the term "radiosensitizer" refers to a compound that enhances the effects of radiation, often by mimicking oxygen, which is a radiation sensitizer. For reviews on bioreductive therapy and synthesis of nitroimidazole prodrugs, see e.g., Jaffar et al. *Adv. Drug Del. Rev.* (2001) 53: 217-28; Naylor, M. A. and P. Thomson *Mini Rev. Med. Chem.* (2001) 1: 17-29; Hay et al. *J. Med. Chem.* (2003) 46: 5533-45.

Chemotherapy (meaning the use of chemical substances to treat or control disease) plays a vital role in killing cancerous cells of solid tumors because of the failure of radiotherapy to do the same. Derivatives of 2-nitroimidazole are used widely as prodrugs in chemotherapy owing to their hypoxia selectivity. For example, some widely used 2-nitroimidazole prodrugs are shown below:

2-Nitroimidazoles: Hypoxia Selective Cytotoxin Prodrugs

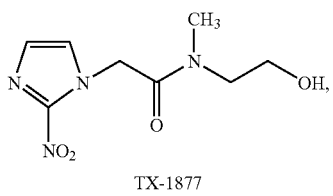

TX-1877

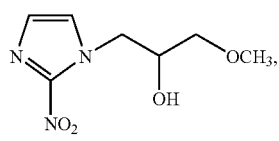

MISO

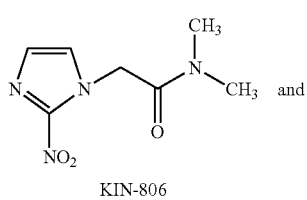

KIN-806 and

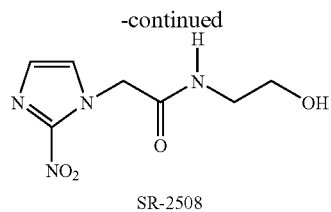

SR-2508 where TX-1877 is N-(2-hydroxyethyl)-2-nitro-1H-imidazole-1-methylacetamide, MISO (misonidazole) is 3-methoxy-1-(2-nitroimidazol-1-yl)-2-propanol, KIN-806 is 2-nitro-1H-imidazole-1-dimethylacetamide, and SR-2508 (etanidazole) is N-(2-hydroxyethyl)-2-nitro-1H-imidazole-1-acetamide.

Although 2-nitroimidazole derivatives have been used widely in chemotherapy for several years, the synthesis of 2-nitroimidazole from an imidazole has been a challenge, likely (i.e., without being bound by a particular theory) because of the challenge posed by the nitration (i.e., the process of incorporating a "nitro" or "—$NO_2$" group in a chemical compound) of imidazole at the second (2)-position.

When subjected to nitration, generally, imidazole gives rise to either a 4-nitroimidazole derivative (2) or a 5-nitroimidazole derivative (3), while the 2-nitroimidazole derivative (1) has remained elusive (structures shown below).

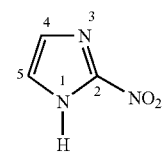

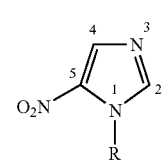

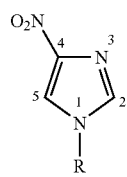

2-, 4-, and 5-nitroimidazoles

The nitration of an imidazole has been accomplished with the use of fuming nitric acid, either in the presence of sulfuric acid or acetic anhydride. These synthesis methods do not result in the formation of 2-nitroimidazole derivatives, but rather, these methods result in the formation of 4-nitroimidazole derivatives or 5-nitroimidazole derivatives, respectively, as outlined in Scheme 1.

Scheme 1: Methods of Nitration of Imidazoles

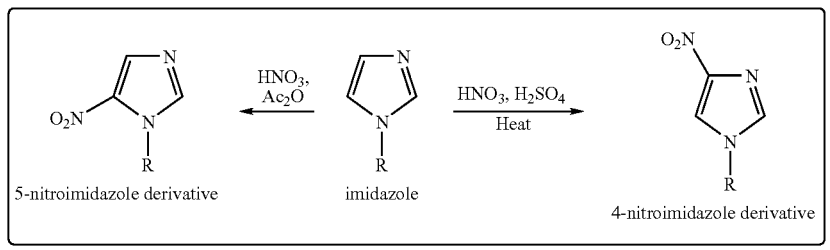

5-nitroimidazole derivative     imidazole     4-nitroimidazole derivative

See Grimmett, M. R. *Heterocyclic Chem.* (1980) 27: 241; Chauviere, G. et al. *J. Med. Chem.* (2003) 46: 427-40.

Often synthesis of 2-nitroimidazoles uses highly acidic conditions, resulting in low yields (e.g., less than about 60%) of the desired imidazole. As used herein, the phrase "highly acidic" refers to substances that generate acid or that inherently are acidic in nature, for example and without limitation, nitric acid, a combination of nitric acid and acetic anhydride, and a combination of nitric acid and sulfuric acid. For example, Chinese Patent No. 1461749 describes producing 2-nitroimidazoles using acid and acid-related reagents (defined hereinbelow): 40% fluoroboric acid, nitrous acid sodium salt (which, in the presence of acids forms nitrous acid), and concentrated hydrochloric acid; Japanese Patent No. 2001122861 describes producing 2-nitroimidazoles (52% yield) using an acid and an acid-related reagent: sulfuric acid and nitrous acid sodium salt; and Wu, Y. et al. describe producing 2-nitroimidazoles using the Sandmeyer reaction, which is known to involve the substitution of an amino group of an aromatic hydrocarbon via preparation of its diazonium salt (the amino group reacts with nitrous oxide under acidic conditions to produce the diazonium salt) with subsequent displacement with a nucleophile (meaning a "nucleus-loving" chemical species, i.e., a negatively charged chemical species).

Also, synthesis of 2-nitroimidazoles using highly acidic conditions is described, for example, by Xiao, Q. et al., who describe producing 2-nitroimidazoles using acid and acid-related reagents: either fluoroboric acid and nitrous acid sodium salt (59% yield) or hydrochloric acid and nitrous acid sodium salt (36% yield) (*Zhongguo Yiyao Gongye Zazhi* (2001) 32(12): 557-58), while Davis et al. describe producing 2-nitroimidazoles involving acid hydrolysis using concentrated hydrochloric acid (18% to 50% yields) (*J. Heterocyclic Chem.* (March-April 1982) 19: 253-56).

Thus, there is a need for a way to synthesize 2-nitroimidazole and its derivatives (collectively referred to herein as "2-nitroimidazoles") that, for example, uses less harsh, more environmentally and user friendly reagents, is less costly with regards to materials (e.g., expense and use), labor and production (i.e., process friendly method for practical use), and provides the compound in acceptable yields, such as, in amounts able to provide a supply of the compound to sustain activities that require a regular, reliable supply of the compound (e.g., a yield of at least about 60%). The present invention is directed to these and other unmet needs.

SUMMARY OF THE INVENTION

The present invention provides a process for making an N-substituted-2-nitroimidazole or a pharmaceutically-acceptable salt thereof the process comprising the steps of:

a. reacting an N-substituted imidazole of formula I:

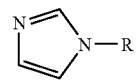

I wherein:
R is halogen, $C_1$-$C_{10}$ alkyl, $C_1$-$C_{10}$ alkenyl, $C_2$-$C_{10}$ alkynyl, alkoxy, alkenoxy, alkynoxy, alkylalkoxy, cycloalkyl, cycloalkenyl, cycloalkynyl, aryl, arylalkyl, alkylaryl, heteroaryl, heterocycloalkyl, heterocycloalkenyl, heterocycloalkynyl, or $C(O)OR^2$, where $R^2$ is $C_1$-$C_{10}$ alkyl, $C_2$-$C_{10}$ alkenyl, $C_2$-$C_{10}$ alkynyl, alkoxy, alkenoxy, alkynoxy, alkylalkoxy, cycloalkyl, cycloalkenyl, cycloalkynyl; wherein:
each $C_1$-$C_{10}$ alkyl, $C_2$-$C_{10}$ alkenyl, $C_2$-$C_{10}$ alkynyl, alkoxy, alkylalkoxy, cycloalkyl, cycloalkenyl, cycloalkynyl aryl, arylalkyl, alkylaryl, heteroaryl, heterocycloalkyl, heterocycloalkenyl or heterocycloalkynyl is, independently, optionally substituted by one or more halogen, hydroxy, alkoxy or phenyl groups,
with the proviso that $C_1$ is not substituted with three phenyl groups,
with a base to produce a mixture; and
b. reacting the mixture with at least one nitrating agent, with the proviso that the nitrating agent is not a non-acidic alkyl nitrate.

In some embodiments of the process of the present invention, the base of step (a) is in the presence of a solvent. In some such embodiments, the solvent comprises tetrahydrofuran, tetrahydropyran, dimethylformamide, diethyl ether or hexane; tetrahydrofuran; or tetrahydropyran.

In some embodiments of the process of the present invention, the base of step (a) comprises a base with a pKa value of at least about 40, a phosphazene base, sodium amide, potassium hexamethyldisilazane, lithium tetramethylpiperidide, diisopropyl ethylamine, butyl lithium, or $R^5Li$, where $R^5$ is at least a $C_4$-alkyl. In some such embodiments, the base comprises butyl lithium, such as, e.g., n-butyl lithium, t-butyl lithium or s-butyl lithium, in some such embodiments, the butyl lithium comprises n-butyl lithium.

In some embodiments of the process of the present invention, the nitrating agent comprises an inorganic nitrate, nitronium tetrafluoroborate or cerric ammonium nitrate. In some such embodiments, the inorganic nitrate comprises ammonium nitrate, barium nitrate, calcium nitrate, lead nitrate, lithium nitrate, magnesium nitrate, potassium nitrate, silver nitrate, sodium nitrate or strontium nitrate.

In some embodiments of the process of the present invention, the inorganic nitrate is in the presence of a carboxylic acid anhydride. In some such embodiments, the carboxylic acid anhydride has a formula of $(R^3CO)_2O$ or $R^3R^4(CO)_2O$, where:

$R^3$ and $R^4$ are each, independently, H, halogen, $C_1$-$C_{10}$ alkyl, $C_2$-$C_{10}$ alkenyl, $C_2$-$C_{10}$ alkynyl, cycloalkyl, aryl, or arylalkyl, where:

each $C_1$-$C_{10}$ alkyl, $C_2$-$C_{10}$ alkenyl, $C_1$-$C_{10}$ alkynyl, cycloalkyl, aryl, or arylalkyl is, independently, optionally substituted by one or more halogen, hydroxyl or alkoxy; or $R^3$ and $R^4$ taken together form an aryl, a cycloalkyl or cycloakenyl.

In some such embodiments, $R^3$ and $R^4$ are each, independently, $C_1$-$C_{10}$ alkyl optionally substituted by one or more halogen, hydroxyl or alkoxy; $R^3$ and $R^4$ are each $C_1$ alkyl optionally substituted by one or more halogen, hydroxyl or alkoxy; or $R^3$ and $R^4$ taken together form a cycloalkyl, cycloakenyl or an aryl. In some such embodiments, $R^3$ and $R^4$ are each, independently, cycloalkyl optionally substituted with one or more halogen, hydroxyl or alkoxy; or $R^3$ and $R^4$ are each, independently, aryl optionally substituted with one or more halogen, hydroxyl or alkoxy. In some embodiments, the carboxylic acid anhydride comprises acetic anhydride, difluoroacetic anhydride, trifluoroacetic anhydride, dichloroacetic anhydride, or trichloroacetic anhydride. In some such embodiments, the carboxylic acid anhydride comprises trifluoroacetic anhydride or trichloroacetic anhydride; or trifluoroacetic anhydride.

In some embodiments of the process of the present invention, the N-substituted-2-nitroimidazole made has a yield of at least about 60%.

The present invention further provides a N-substituted-2-nitroimidazole made according to the process of the present invention.

DETAILED DESCRIPTION OF THE INVENTION

Definitions. In describing the present invention, the following terms and phrases will be used and are intended to be defined as indicated immediately below. Definitions for other terms and phrases can occur throughout the specification. It is intended that all terms and phrases used in the specification include the plural, active tense and past tense forms of a term or a phrase.

As used herein, the term "acid" refers to a compound that can be characterized by one of three chemical concepts: (1) it lowers the pH (increases the hydrogen ion concentration) when added to an aqueous solution, (2) it acts as a proton donor in solution, or (3) it can accept a pair of electrons to form a covalent bond.

As used herein, the term "acid-related" refers to a compound that is of, being, or having the reactions or characteristics of, an acid, or derived by partial exchange of replaceable hydrogen (e.g., a salt or ester of an acid).

As used herein, the term "alkyl" refers to a saturated hydrocarbon group that is unbranched (i.e., straight-chained) or branched (i.e., non-straight chained). Example alkyl groups, without limitation, include methyl (Me), ethyl (Et), propyl (e.g., n-propyl and isopropyl), butyl (e.g., n-butyl, isobutyl, t-butyl), pentyl (e.g., n-pentyl, isopentyl, neopentyl), and the like. In some embodiments of the present invention, an alkyl group can contain from about 1 to about 10, from about 2 to about 8, from about 3 to about 6, from about 1 to about 8, from about 1 to about 6, from about 1 to about 4, from about 1 to about 3 carbon atoms, or from about 1, 2, 3, 4, 5, 6, 7, 8, 9 or 10 carbon atoms.

As used herein, the term "alkylalkoxy" refers to an unbranched or branched alkyl group (defined herein) having been substituted with at least one alkoxy group (defined herein).

As used herein, the term "alkylaryl" or "alkaryl" is intended to denote an aryl group (defined herein) that bears an alkyl substituent (defined herein); for example, and without limitation, a 4-methylphenyl group.

As used herein, the term "alkenoxy" refers to an alkenyl-O— group, where the term "alkenyl" is as defined herein. Example alkenoxy groups include, without limitation, vinyloxy, allyloxy, 3-methyl-2-propenoxy and the like.

As used herein, the term "alkenyl" refers to an unsaturated branched or unbranched hydrocarbon group having at least one double carbon-carbon (—C═C—) bond. Example alkenyl groups include, without limitation, ethenyl, 1-propenyl, isopropenyl, 2-butenyl, 1,3-butadienyl, 3-pentenyl and 2-hexenyl, and the like. In some embodiments of the present invention, an alkenyl group can contain from 2 to about 10, from 2 to about 8, from 2 to about 6, from 2 to about 4, from about 3 to about 6 carbon atoms, or from 2, 3, 4, 5, 6, 7, 8, 9 or 10 carbon atoms.

As used herein, the term "alkoxy" refers to an alkyl-O— group, where the term "alkyl" is defined herein. Example alkoxy groups include, without limitation, methoxy, ethoxy, propoxy (e.g., n-propoxy and isopropoxy), t-butoxy, and the like.

As used herein, the term "alkynoxy" refers to an alkynyl-O— group, where the term "alkynyl" is defined herein. Example alkynoxy groups include, without limitation, propargyloxy, 2-butynyloxy and the like.

As used herein, the term "alkynyl" refers to a branched or unbranched hydrocarbon group having at least one triple carbon-carbon (—C≡C—) bond. Example alkynyl groups include, without limitation, ethynyl, 1-propynyl, 2-propynyl, 2-butynyl, 3-butynyl, 2-penten-4-ynyl, and the like. In some embodiments of the present invention, an alkynyl group can contain from about 2 to about 10, from about 2 to about 8, from about 2 to about 6, from about 2 to about 4, from about 3 to about 6 carbon atoms, or from about 2, 3, 4, 5, 6, 7, 8, 9 or 10 carbon atoms.

As used herein, the term "amino" refers to the monovalent group —$NH_2$.

As used herein, the term "aryl" refers to a monocyclic or polycyclic (e.g., having 2, 3 or 4 fused rings) aromatic hydrocarbon group, for example, and without limitation, phenyl, naphthyl, anthracenyl, phenanthrenyl, indanyl, indenyl, and the like. In some embodiments of the present invention, an aryl group can have from about 6 to about 20 carbon atoms.

As used herein, the term "aminoaryl" refers to an aryl group, as defined herein, substituted with an amino group, as defined herein.

As used herein, the term "arylalkyl" or "aralkyl" refers to an alkyl group (defined herein) that bears an aryl (defined herein) substituent; for example, and without limitation, a benzyl group.

As used herein, the term "base" refers to a compound that is an electron rich species that reacts with acidic hydrogen (i.e., the compound has an affinity for protons).

As used herein, the phrase "chemical reaction" refers to a process that results in the interconversion of chemical species (e.g., an atom, molecule, molecular fragment or ion). A chemical reaction can be an "elementary reaction" (meaning a chemical reaction where no reaction intermediates are detectable or need be postulated to describe the reaction on a molecular scale) or a "stepwise reaction" (meaning a chemical reaction with at least one reaction intermediate and involving at least two elementary reactions). (See e.g., the International Union of Pure and Applied Chemistry (IUPAC) Compendium of Chemical Terminology, $2^{nd}$ ed. (1997), hereinafter, "IUPAC".)

As used herein, the term "cycloalkyl" refers to a saturated cyclic hydrocarbon group (i.e., a cyclized alkyl group). Cycloalkyl groups can include mono- or polycyclic (e.g., having 2, 3 or 4 fused rings) ring systems as well as spiro ring systems. Ring-forming carbon atoms of a cycloalkyl group optionally can be substituted by oxo or sulfido. Example cycloalkyl groups include, for example, cyclopropyl, cyclobutyl, cyclopentyl, cyclohexyl, cycloheptyl, 1-decalinyl, norbornyl, adamantyl and the like. Also included in the definition of cycloalkyl are moieties that have one or more aromatic rings (can be aryl or heteroaryl) fused (i.e., having a bond in common with) to the cycloalkyl ring; for example, and without limitation, benzo or thienyl derivatives of pentane, hexane, and the like.

As used herein, the term "cycloalkenyl" refers a cyclic hydrocarbon group having at least one double carbon-carbon (—C═C—) bond (i.e., a cyclized alkenyl group). Cycloalkenyl groups can include mono- or polycyclic (e.g., having 2, 3 or 4 fused rings) ring systems as well as spiro ring systems. Ring-forming carbon atoms of a cycloalkenyl group optionally can be substituted by oxo or sulfido. Example cycloalkenyl groups include, and without limitation, cyclopentenyl, cyclohexenyl, cyclohexadienyl, cycloheptatrienyl, and the like. Also included in the definition of cycloalkyl are moieties that have one or more aromatic rings (can be aryl or heteroaryl) fused (i.e., having a bond in common with) to the cycloalkyl ring; for example, and without limitation, benzo or thienyl derivatives of pentene, hexene, and the like.

As used herein, the term "cycloalkynyl" refers to a cyclic hydrocarbon group having at least one triple carbon-carbon (—C≡C—) bond (i.e., a cyclized alkynyl group). Cycloalkenyl groups can include mono- or polycyclic (e.g., having 2, 3 or 4 fused rings) ring systems as well as spiro ring systems. Ring-forming carbon atoms of a cycloalkenyl group optionally can be substituted by oxo or sulfido. Example cycloalkynyl groups include, without limitation, pentynyl, hexynyl and the like.

As used herein, "halogen" refers to a monovalent, nonmetallic element, including fluorine, chlorine, bromine, and iodine.

As used herein, the term "heteroaryl" refers to an aromatic heterocycle of 3 to 20 atoms having at least one heteroatom ring member such as sulfur, oxygen, or nitrogen, which is a monocyclic or polycyclic (e.g., having 2, 3 or 4 fused rings) system. Examples of heteroaryl groups include without limitation, 5-membered heteroaryl groups such as furyl, triazolyl, thienyl, pyrrolyl, thiazolyl, isothiazolyl, imidazolyl, pyrazolyl, isoxazolyl and the like; 6-membered heteroaryl groups, such as pyridyl, pyrimidinyl, pyrazinyl, pyridazinyl, morpholinyl and the like and the N-oxides thereof; and polycyclic systems that are benzo-fused ring systems derived from the heteroaryl groups named above, e.g. quinolyl, isoquinolyl, phthalazinyl, quinazolinyl, benzofuranyl, benzothienyl, benzodioxolyl, indolyl and the like. In some embodiments of the present invention, the heteroaryl group has from about 1 to about 20 carbon atoms, and in some embodiments from about 3 to about 20 carbon atoms. In some embodiments of the present invention, the heteroaryl group contains about 3 to about 14, about 3 to about 7, or about 5 to about 6 ring-forming atoms. In some embodiments of the present invention, the heteroaryl group contains 5 to 6 ring-forming atoms. In some embodiments of the present invention, the heteroaryl group has about 1 to about 4, about 1 to about 3, or about 1 to 2 heteroatoms.

As used herein, "heterocycloalkyl" refers to non-aromatic saturated heterocycles (i.e., cyclized alkyls) where one or more of the ring-forming carbon atoms is replaced by a heteroatom, such as an oxygen, nitrogen, or sulfur atom, which include mono- or polycyclic (e.g., having 2, 3 or 4 fused rings) ring systems as well as spiro ring systems. Example heterocycloalkyl groups include, without limitation, 1,3-dioxolanyl, morpholinyl, thiomorpholinyl, tetrahydrofuranyl, tetrahydrothienyl, piperidinyl, piperazinyl, pyrrolidinyl, pyrazolidinyl, oxazolidinyl, isoxazolidinyl, thiazolidinyl, isothiazolidinyl, imidazolidinyl, and the like. Also included in the definition of heterocycloalkyl are moieties that have one or more aromatic rings (can be aryl or heteroaryl) fused (i.e., having a bond in common with) to the nonaromatic heterocyclic ring, for example 2,3-dihydrobenzofuryl, 1,3-benzodioxole, benzo-1,4-dioxane, phthalimidyl, naphthalimidyl, 4,5,6,7-tetrahydrothieno[2,3-c]pyridinyl, and benzo derivatives of heterocycles such as 1,2,3,4-tetrahydroisoquinyl, indolene and isoindolene groups. Ring-forming carbon atoms and heteroatoms of a heterocycloalkyl group can be optionally substituted by oxo or sulfido. In some embodiments of the present invention, the heterocycloalkyl group has from about 1 to about 20 carbon atoms, and in further embodiments from about 3 to about 20 carbon atoms. In some embodiments, the heterocycloalkyl group contains about 3 to about 14, about 3 to about 7, or about 5 to about 6 ring-forming atoms. In some embodiments of be present invention, the heterocycloalkyl group contains about 5 to about 6 ring-forming atoms. In some embodiments of the present invention, the heterocycloalkenyl group has about 1 to about 4, about 1 to about 3, or about 1 to about 2 heteroatoms.

As used herein, "heterocycloalkenyl" refers to unsaturated non-aromatic heterocycles having at least one double carbon-carbon (—C═C—) bond and where one or more of the ring-forming carbon atoms is replaced by a heteroatom, such as an oxygen, nitrogen, or sulfur atom. Heterocycloalkenyl groups include mono- or polycyclic (e.g., having 2, 3 or 4 fused rings) ring systems as well as spiro ring systems. In some embodiments of the present invention, the heterocycloalkyl group has from about 1 to about 20 carbon atoms, and in further embodiments from about 3 to about 20 carbon atoms. In some embodiments of the present invention, the heterocycloalkyl group contains about 3 to about 14, about 3 to about 7, or about 5 to about 6 ring-forming atoms. In some embodiments of the present invention, the heterocycloalkyl group contains about 5 to about 6 ring-forming atoms. In some embodiments of the present invention, the heterocycloalkenyl group contains about 1 to about 3 double bonds. In some embodiments of the present invention, the heterocycloalkenyl group has about 1 to about 4, about 1 to about 3, or about 1 to about 2 heteroatoms.

As used herein, "heterocycloalkynyl" refers to unsaturated non-aromatic heterocycles having at least one triple carbon-carbon (—C≡C—) bond and where one or more of the ring-forming carbon atoms is replaced by a heteroatom, such as an oxygen, nitrogen, or sulfur atom. Heterocycloalkenyl groups include mono- or polycyclic (e.g., having 2, 3 or 4 fused rings) ring systems as well as spiro ring system. In some embodiments of the present invention, the heterocycloalkyl group has from about 1 to about 20 carbon atoms, and in further embodiments from about 3 to about 20 carbon atoms. In some embodiments, the heterocycloalkyl group contains about 3 to about 14, about 3 to about 7, or about 5 to about 6 ring-forming atoms. In some embodiments, the heterocycloalkyl group contains about 5 to about 6 ring-forming atoms. In some embodiments of the present invention, the heterocycloalkynyl group contains about 1 to about 2 triple bonds. In some embodiments of the present invention, the heterocycloalkenyl group has about 1 to about 4, about 1 to about 3, or about 1 to about 2 heteroatoms.

As used herein, the term "mixture" refers to a blending together of two or more substances without the occurrence of a chemical reaction by which the substances would lose their individual properties, i.e., without the permanent gain or loss of electrons.

As used herein, the phrase "nitrating agent" refers to a compound that introduces a nitro group ($-NO_2$) onto a carbon atom of another compound.

As used herein, the phrase "reaction intermediate" refers to a molecular entity with a lifetime appreciably longer than a molecular vibration (corresponding to a local potential energy minimum of depth greater than RT, which is the product of the molar gas constant, R, and the temperature, T) that is formed (directly or indirectly) from the reactants and reacts further to give (either directly or indirectly) the products of a chemical reaction (see e.g., IUPAC).

As used herein, the phrase "reaction stage" refers to a set of one or more (possibly, inseparable experimentally) reaction steps (as defined herein) leading to and/or from a detectable or presumed reaction intermediate (see e.g., IUPAC).

As used herein, the phrase "reaction step" refers to an elementary reaction constituting one of the stages of a stepwise reaction in which a reaction intermediate (or, for the first step, the reactants) is converted into the next reaction intermediate (or, for the last step, the products) in the sequence of reaction intermediates between reactants and products (see e.g., IUPAC).

As used herein, the terms "react," "reacted" and "reacting" mean undergoing a chemical reaction, as defined herein.

As used herein, the phrases "selective substitution" and "selectively substituted" refer to specifically altering a compound by introduction of a substituent (defined herein), usually, at a specific location of the compound.

As used herein, the term "substituent" refers to an atom or group of bonded atoms that can be considered to have replaced a hydrogen atom in a compound.

In one aspect, the present invention provides a process for making an N-substituted-2-nitroimidazole or pharmaceutically-acceptable salt thereof. In some embodiments, the process for making an N-substituted-2-nitroimidazole, or a pharmaceutically-acceptable salt thereof, comprises (a) reacting an N-substituted imidazole of formula I:

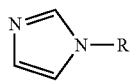

I where:
R is halogen, $C_1$-$C_{10}$ alkyl, $C_2$-$C_{10}$ alkenyl, $C_2$-$C_{10}$ alkynyl, alkoxy, alkenoxy, alkynoxy, alkylalkoxy, cycloalkyl, cycloalkenyl, cycloalkynyl, aryl, aryl alkyl, alkylaryl, heteroaryl, heterocycloalkyl, heterocycloalkenyl, heterocycloalkynyl, or C(O)OR$^2$, where R$^2$ is $C_1$-$C_{10}$ alkyl, $C_2$-$C_{10}$ alkenyl, $C_2$-$C_{10}$ alkynyl, alkoxy, alkenoxy, alkynoxy, alkylalkoxy, cycloalkyl, cycloalkenyl, cycloalkynyl;

wherein:
each $C_1$-$C_{10}$ alkyl, $C_2$-$C_{10}$ alkenyl, $C_2$-$C_{10}$ alkynyl, alkoxy, alkylalkoxy, cycloalkyl, cycloalkenyl, cycloalkynyl, aryl, arylalkyl, alkylaryl, heteroaryl, heterocycloalkyl, heterocycloalkenyl or heterocycloalkynyl is, independently, optionally substituted by one or more halogen, hydroxy, alkoxy or phenyl groups,
with the proviso that $C_1$ is not substituted with three phenyl groups, with a base to produce a mixture, and (b) reacting the mixture with at least one nitrating agent, with the proviso that the nitrating agent is not a non-acidic alkyl nitrate.

In the present invention, without being bound by any particular theory, N-substituted imidazole undergoes selective substitution at the 2-position as shown in Scheme 2:

Scheme 2: Electrophilic Substitution of Imidazoles in Basic Conditions

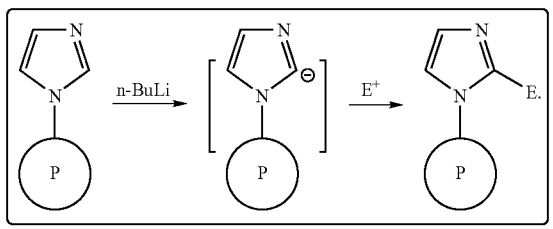

Such synthesis involves treatment of a protected imidazole with a strong base followed by reacting with an electrophile (meaning an "electron-loving" chemical species, i.e., a positively charged chemical species). As used herein, the term "protected imidazole," refers to an imidazole where the characteristic chemistry of a functional group of the imidazole has been masked with another group ("a protecting group") during a chemical reaction because the functional group interferes with the chemical reaction, thereby allowing another functional group of the imidazole an opportunity to react. As used herein, the phrase "strong base" refers to a base whose pKa value is greater than or equal to 40 (i.e., pKa≧40).

Without being bound by any particular theory, when a 2-nitroimidazole is synthesized under highly acidic conditions, such conditions destabilize the chemical intermediate, which can lead to nitration at C-2 of the chemical intermediate (Scheme 3) and hence, failure in obtaining the desired 2-nitroimidazole product; because under highly acidic conditions, C-2 of the chemical intermediate is severely electron depleted in comparison to C-4 or C-5 of the chemical intermediate. Yet, if the conditions are made Scheme 3: Resonance Contributors for Imidazole Disfavoring 2-Nitration

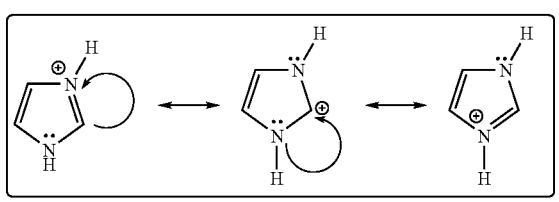

basic, C-2 of the imidazole bears the most acidic hydrogen and will give away a proton, thereby forming a chemical intermediate that is a negatively charged anion. The resulting anion, if reacted with a neutral nitrating species, is expected to result in the desired 2-substitution of the imidazole product (Scheme 2).

In some embodiments, the process of the present invention for making an N-substituted nitroimidazole comprises a base that is in the presence of a solvent, in some embodiments, the solvent of the process of the present invention comprises tetrahydrofuran, tetrahydropyran, dimethylformamide, diethyl ether or hexane. In some embodiments, the solvent of the process of the present invention comprises tetrahydrofuran; in some embodiments, the solvent comprises tetrahydropyran.

In some embodiments, the process of the present invention for making an N-substituted nitroimidazole comprises abase with a pKa value of at least about 40, a phosphazene base, sodium amide or sodamine ($NaNH_2$), potassium hexamethyldisilazane (KHMDS, $C_6H_{18}KNSi_2$), lithium tetramethylpiperidide (LiTMP), diisopropyl ethyl amine, butyl lithium (BuLi, $C_4H_9Li$), or RLi, where R is at least a $C_4$-alkyl, i.e., R is an alkyl comprising four or more carbon atoms.

In some embodiments, the base of the process of the present invention has a pKa value of at least about 40. In some embodiments, the base of the process of the present invention comprises a phosphazene base. Phosphazene bases suitable for the present invention include, without limitation, phosphazene bases manufactured by Sigma Aldrich (St. Louis, Mo.).

In some embodiments, the phosphazene base of the process of the present invention comprises bis[tris(dimethylamino)phosphoranylidene]ammonium fluoride (phosphazenium fluoride; $P_2$—F; $C_{12}H_{36}FN_7P_2$), 1-tert-butyl-4,4,4-tris(dimethylamino)-2,2-bis[tris(dimethylamino)-phosphoranyldenamino]-$2A^5,4A^5$-catenadi(phosphazene) (phosphazene base $P_4$-t-Bu; $C_{22}H_{63}N_{13}P_4$), 1-tert-octyl-4,4,4-tris(dimethylamino)-2,2-bis[tris(dimethylamino)phosphoranylidenamino]-$2A^5,4A^5$-catenadi(phosphazene) (phosphazene base $P_4$-t-Oct; $C_{26}H_{71}H_{13}P_4$), or tetrakis[tris(dimethylamino)phosphoranylidenamino]phosphonium fluoride (phosphazenium fluoride $P_5$—F; $C_{24}H_{72}FN_{16}P_5$). In some embodiments, the phosphazene base of the process of the present invention comprises about four (4) phosphor atoms; in some embodiments, the phosphazene base comprises about five (5) phosphor atoms.

In some embodiments, the base of the process of the present invention comprises butyl lithium. In some embodiments, the butyl lithium of the process of the present invention comprises normal butyl lithium (n-butyl lithium), tertiary butyl lithium (tert- or t-butyl lithium) or secondary butyl lithium (sec- or s-butyl lithium). In some embodiments, the base of the process of the present invention comprises n-butyl lithium.

In some embodiments, the nitrating agent of the process of the present invention is neutral. As used herein, the term "neutral" refers to having no net electrical charge, or providing, containing, or relating to equal concentrations of hydrogen ions ($H^+$) and hydroxide ions ($OH^-$). In some embodiments, the nitrating agent of the process of the present invention comprises an inorganic nitrate, nitronium tetrafluoroborate or cerric ammonium nitrate.

In some embodiments, the inorganic nitrate of the process of the present invention comprises ammonium nitrate ($NH_4NO_3$), barium nitrate ($Ba(NO_3)_2$), calcium nitrate ($Ca(NO_3)_2 \cdot 4H_2O$), lead nitrate ($Pb(NO_3)_2$), lithium nitrate ($LiNO_3$), magnesium nitrate ($MgNO_3$), potassium nitrate ($KNO_3$), silver nitrate ($AgNO_3$), sodium nitrate ($NaNO_3$) or strontium nitrate ($SrNO_3$). In some embodiments, the inorganic nitrate of the process of the present invention is potassium nitrate.

In some embodiments, the inorganic nitrate of the process of the present invention is in the presence of a carboxylic acid or a carboxylic acid anhydride.

In some embodiments, the inorganic nitrate of the process of the present invention is in the presence of a carboxylic acid anhydride. In some embodiments, the carboxylic acid anhydride has a formula of $(R^3CO)_2O$ or $R^3R^4(CO)_2O$:
  wherein $R^3$ and $R^4$ are each, independently, H, halogen, $C_1$-$C_{10}$ alkyl, $C_2$-$C_{10}$ alkenyl, $C_2$-$C_{10}$ alkynyl, cycloalkyl, aryl, or aryl alkyl,
    wherein each $C_1$-$C_{10}$ alkyl, $C_2$-$C_{10}$ alkenyl, $C_1$-$C_{10}$ alkynyl, cycloalkyl, aryl, or arylalkyl is, independently, optionally substituted by one or more halogen, hydroxyl or alkoxy; or
  wherein $R^3$ and $R^4$ taken together form an aryl, a cycloalkyl or cycloakenyl.

In some embodiments, the carboxylic acid anhydride of the process of the present invention comprises $R^3$ and $R^4$ groups that are each, independently, $C_1$-$C_{10}$ alkyl optionally substituted by one or more halogen, hydroxyl or alkoxy. In some embodiments, $R^3$ and $R^4$ of the carboxylic acid anhydride are each $C_1$ alkyl (i.e., a methyl group) optionally substituted by one or more halogen, hydroxyl or alkoxy.

In some embodiments, the carboxylic acid anhydride of the process of the present invention comprises acetic anhydride, difluoroacetic anhydride (DFAA), trifluoroacetic anhydride (TFAA), dichloroacetic anhydride (DCAA), or trichloroacetic anhydride (TCAA). In some embodiments, the carboxylic acid anhydride comprises trifluoroacetic anhydride or trichloroacetic anhydride. In some embodiments, the carboxylic acid anhydride comprises trifluoroacetic anhydride.

In some embodiments, the carboxylic acid anhydride of the process of the present invention comprises $R^3$ and $R^4$ groups that taken together form a cycloalkyl, cycloakenyl or an aryl.

In some embodiments, the carboxylic acid anhydride of the process of the present invention comprises malonic acid anhydride, succinic acid anhydride, maleic acid anhydride, lactic acid anhydride, phthalic acid anhydride, isophthalic acid anhydride or terephthalic acid anhydride.

In some embodiments, the carboxylic acid anhydride of the process of the present invention comprises $R^3$ and $R^4$ groups that are each, independently, cycloalkyl optionally substituted with one or more halogen, hydroxyl or alkoxy. In some such embodiments, $R^3$ and $R^4$ are each cyclohexane. In some embodiments, the carboxylic acid anhydride of the process of the present invention comprises cyclohexanecarboxylic acid anhydride.

In some embodiments, the carboxylic acid anhydride of the process of the present invention comprises $R^3$ and $R^4$ groups that are each, independently, aryl optionally substituted with one or more halogen, hydroxyl or alkoxy. In some such embodiments, $R^3$ and $R^4$ are each benzoic acid. In some embodiments, the carboxylic acid anhydride of the process of the present invention comprises benzoic acid anhydride.

In some embodiments, the process of the present invention provides the N-substituted-2-imidazole in a yield less than or equal to about 40% (i.e., $\leq 40\%$). Without being bound by any particular theory, such embodiments can comprise a nitrating agent in the presence of a carboxylic acid; i.e., in the presence of a carboxylic acid, the nitrating agent is less successful in generating the active nitrating species compared to when the nitrating agent is in the presence of an anhydride derivative of the carboxylic acid).

In some embodiments, the process of the present invention provides the N-substituted-2-nitroimidazole in a yield of at least about 60% (i.e., ≦60%). In some embodiments, the yield of N-substituted-2-nitroimidazole is at least about 65%; at least about 70%; at least about 75%; at least about 80%; at least about 85%; at least about 90%.

In some embodiments of the process of the present invention, the yield of N-substituted-2-nitroimidazole is from about 60% to about 100% (inclusive of each endpoint). In some embodiments of the process of the present invention, the yield of N-substituted-2-nitroimadazole is from about 60% to about 90% (inclusive of each endpoint). In some embodiments, the yield of M-substituted-2-nitroimidazole is from about 60% to about 75% (inclusive of each endpoint).

The process for making N-substituted-2-nitroimidazoles of the present invention is direct, meaning the process: (1) is straightforward, (2) has a fast reaction time (e.g., at least about 15 minutes and no more than about 30 minutes), and (3) has little or no isolation or removal of extraneous compounds or reaction intermediates during the chemical reaction, or has a small number (e.g., about 1 to about 3) of reaction stages and/or reaction steps (i.e., the process is not a multistep or multistage process meaning having multiple steps or stages).

In some embodiments, the process of the present invention for making N-substituted-2-nitroimidazoles occurs in one to about two reaction stages. In some embodiments, the process of the present invention occurs in one reaction stage. In some embodiments, the process of the present invention for making N-substituted-2-nitroimidazoles occurs in about two reaction steps (e.g., reactions steps (a) and (b), as described above). In some embodiments, the process of the present invention occurs in one stage and two reaction steps, i.e., in one stage comprising two reaction steps.

In some embodiments, the process for making N-substituted-2-nitroimadazole of the present invention has a reaction time of about 15 to about 30 minutes (inclusive of the endpoints). In some embodiments, the reaction time is at least about 15 minutes; at least about 20 minutes; at least about 25 minutes; or at least about 30 minutes.

The process for making N-substituted-2-imidazoles of the present invention is performed at a low temperature, such as from about 0° C. to about 10° C. In some embodiments, the process is performed at a temperature that is at least about 4° C. In some embodiments of the process of the present invention, an active nitrating species is generated in situ at about 4° C.

In some embodiments, the process for making N-substituted-2-nitroimidazoles of the present invention occurs in an absence of an acid. In some embodiments, the process of the present invention occurs in an acid-free environment, i.e. in the absence of an acid or acid-related compound.

In another aspect, the present invention provides a N-substituted-2-nitroimidazole made according to the process of the present invention, as described herein. The N-substituted-2-nitroimidazole made according to the process of the present invention can be isolated and purified by isolation and purification processes and methods known to one of ordinary skill in the art.

Unless defined otherwise, all technical and scientific terms used herein have the same meaning as commonly understood by one of ordinary skill in the art to which this invention belongs. The present invention encompasses any processes and materials similar or equivalent to those described herein and it is not limited to those processes and materials described herein. All publications mentioned herein are incorporated herein by reference to disclose and described the methods and/or materials in connection with which the publications are cited.

It must be noted that, as used herein and in the appended claims, the singular forms "a", "and", and "the" include plural references, unless the context clearly dictates otherwise. All technical and scientific terms used herein have the same meaning when used.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be confirmed independently.

EXAMPLES

The following examples are put forth so as to provide those of ordinary skill in the art with a complete disclosure and description of how to make and use the present, invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.), but an account for some experimental errors and deviations should be made. Unless indicated otherwise, parts are parts by weight, molecular weight is average molecular weight, and temperature is in degrees Centigrade.

Example 1

Preparation of 1-formyl-2-nitro-1H-imidazole 1-formyl-imidazole (about 0.100 grams) was dissolved in 1 mL of tetrahydrofuran at room temperature. Immediately, 1 equivalent (eq.) of n-butyl lithium in about 1.6 M (molar) hexanes was added to the reaction mixture, followed by 1.2 eq. of freshly prepared 1:1 molar mixture of potassium nitrate ($KNO_3$) and trifluoroacetic anhydride (TFAA) in tetrahydrofuran as solvent at about 0° C. to about 4° C. The active nitrating species ($CF_3C(O)ONO_2$), thus, was generated in situ and the reaction mixture was stirred further for about 1.5 minutes. The 1-formyl-2-nitro-1H-imidazole product was isolated and purified by flash column chromatography to yield the pure product (i.e., about 95% purity) in about 62% yield. The structure of the 1-formyl-2-nitro-1H-imidazole product was confirmed by $^1$H NMR spectroscopy. $^1$H NMR ($CDCl_3$): δ 2.8 (s, 3H), 7.20 (d, 1H), 7.74 (d, 1H).

Example 2

Preparation of 1-(p-toluene sulfonyl)-2-nitro-1H-imidazole 1-(toluene sulfonyl)-2-nitro-1H-imidazole was prepared as described in Example 1, except that 1-(p-toluene sulfonyl) imidazole was used rather than 1-formyl-imidazole. The 1-(p-toluene sulfonyl)-2-nitro-1H-imidazole product was isolated and purified by flash column chromatography; 72% yield.

Example 3

Prophetic Synthesis Example

An N-substituted imidazole, wherein the substitutent(s) is inherently non-acidic and/or has a non-acidic hydrogen(s), can be subjected to the nitration method described in Example 1. Upon nitration, the appropriate N-substituted imidazole then can be purified by flash column chromatography to yield the appropriate N-substituted-2-nitro-1H-imidazole in about 60% to about 75% yield.

While the present invention has been described with respect to what are some embodiments of the invention, it is to be understood that the invention is not limited to the disclosed embodiments. To the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. A process for making an N-substituted-2-nitroimidazole or a pharmaceutically-acceptable salt thereof, the process comprising:
   a. reacting an N-substituted imidazole of formula I:

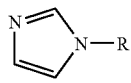

wherein:
      R is halogen, $C_1$-$C_{10}$ alkyl, $C_2$-$C_{10}$ alkenyl, $C_2$-$C_{10}$ alkynyl, alkoxy, alkenoxy, alkynoxy, alkylalkoxy, cycloalkyl, cycloalkenyl, cycloalkynyl, aryl, arylalkyl, alkylaryl, heteroaryl, heterocycloalkyl, heterocycloalkenyl, heterocycloalkynyl, or $C(O)OR^2$, where $R^2$ is $C_1$-$C_{10}$ alkyl, $C_2$-$C_{10}$ alkenyl, $C_2$-$C_{10}$ alkynyl, alkoxy, alkenoxy, alkynoxy, alkylalkoxy, cycloalkyl, cycloalkenyl, cycloalkynyl;
      wherein:
         each $C_1$-$C_{10}$ alkyl, $C_2$-$C_{10}$ alkenyl, $C_2$-$C_{10}$ alkynyl, alkoxy, alkylalkoxy, cycloalkyl, cycloalkenyl, cycloalkynyl, aryl, arylalkyl, alkylaryl, heteroaryl, heterocycloalkyl, heterocycloalkenyl or heterocycloalkynyl is, independently, optionally substituted by one or more halogen, hydroxy, alkoxy or phenyl groups,
            with the proviso that $C_1$ is not substituted with three phenyl groups,
   with a base to produce a mixture; and
   b. reacting the mixture with at least one nitrating agent, with the proviso that the nitrating agent is not a non-acidic alkyl nitrate.

2. The process according to claim 1, wherein the base is in the presence of a solvent.

3. The process according to claim 2, wherein the solvent comprises tetrahydrofuran, tetrahydropyran, dimethylformamide, diethyl ether or hexane.

4. The process according to claim 3, wherein the solvent comprises tetrahydrofuran.

5. The process according to claim 3, wherein the solvent comprises tetrahydropyran.

6. The process according to claim 5, wherein the base comprises a base with a pKa value of at least about 40, a phosphazene base, sodium amide, potassium hexamethyldisilazane, lithium tetramethylpiperidide, diisopropyl ethylamine, butyl lithium, or $R^5Li$, where $R^5$ is at least a $C_4$-alkyl.

7. The process according to claim 6, wherein the base comprises butyl lithium.

8. The process according to claim 7, wherein the butyl lithium comprises n-butyl lithium, t-butyl lithium or s-butyl lithium.

9. The process according to claim 8, wherein the butyl lithium comprises n-butyl lithium.

10. The process according to claim 1, wherein the nitrating agent comprises an inorganic nitrate, nitronium tetrafluoroborate or cerric ammonium nitrate.

11. The process according to claim 10, wherein the inorganic nitrate comprises ammonium nitrate, barium nitrate, calcium nitrate, lead nitrate, lithium nitrate, magnesium nitrate, potassium nitrate, silver nitrate, sodium nitrate or strontium nitrate.

12. The process according to claim 10, wherein the inorganic nitrate is in the presence of a carboxylic acid anhydride.

13. The process according to claim 12, wherein the carboxylic acid anhydride has a formula of $(R^3CO)_2O$ or $R^3R^4(CO)_2O$, wherein:
   $R^3$ and $R^4$ are each, independently, H, halogen, $C_1$-$C_{10}$ alkyl, $C_2$-$C_{10}$ alkenyl, $C_2$-$C_{10}$ alkynyl, cycloalkyl, aryl, or arylalkyl, wherein:
      each $C_1$-$C_{10}$ alkyl, $C_2$-$C_{10}$ alkenyl, $C_2$-$C_{10}$ alkynyl, cycloalkyl, aryl, or arylalkyl is, independently, optionally substituted by one or more halogen, hydroxyl or alkoxy; or
      $R^3$ and $R^4$ taken together form an aryl, a cycloalkyl or cycloakenyl.

14. The process according to claim 13, wherein $R^3$ and $R^4$ are each, independently, $C_1$-$C_{10}$ alkyl optionally substituted by one or more halogen, hydroxyl or alkoxy.

15. The process according to claim 14, wherein $R^3$ and $R^4$ are each $C_1$ alkyl optionally substituted by one or more halogen, hydroxyl or alkoxy.

16. The process according to claim 15, wherein the carboxylic acid anhydride comprises acetic anhydride, difluoroacetic anhydride, trifluoroacetic anhydride, dichloroacetic anhydride, or trichloroacetic anhydride.

17. The process according to claim 16, wherein the carboxylic acid anhydride comprises trifluoroacetic anhydride or trichloroacetic anhydride.

18. The process according to claim 17, wherein the carboxylic acid anhydride comprises trifluoroacetic anhydride.

19. The process according to claim 13, wherein $R^3$ and $R^4$ taken together form a cycloalkyl, cycloakenyl or an aryl.

20. The process according to claim 14, wherein $R^3$ and $R^4$ are each, independently, cycloalkyl optionally substituted with one or more halogen, hydroxyl or alkoxy.

21. The process according to claim 13, wherein $R^3$ and $R^4$ are each, independently, aryl optionally substituted with one or more halogen, hydroxyl or alkoxy.

22. The process according to claim 1, wherein the N-substituted-2-nitroimidazole made has a yield of at least about 60%.

* * * * *